United States Patent [19]

Labovitz et al.

[11] Patent Number: 5,183,891

[45] Date of Patent: Feb. 2, 1993

[54] METHOD FOR THE PREPARATION OF SUBSTITUTED 1,4-DIHYDRO-4-OXO-CINNOLINE-3-CARBOXYLIC ACID, ESTERS AND SALTS THEREOF, AND INTERMEDIATES USED IN THEIR PREPARATION

[75] Inventors: Jeffrey Labovitz, Palo Alto; William J. Guilford, San Leandro; Lawrence Fang, Foster City; Yi Liang, San Jose, all of Calif.

[73] Assignees: Orsan; Orsem, both of Paris, France

[21] Appl. No.: 434,077

[22] Filed: Nov. 9, 1989

[51] Int. Cl.$^5$ .................................. C07D 237/28
[52] U.S. Cl. .................................. 544/235; 560/51; 560/53; 562/459; 562/463; 564/251
[58] Field of Search ................... 544/234, 235

[56] References Cited

U.S. PATENT DOCUMENTS

| 2,797,218 | 6/1957 | Barber et al. | 544/235 |
|---|---|---|---|
| 3,278,604 | 10/1966 | Hoffman et al. | 564/399 |
| 3,320,320 | 5/1967 | Kamlet et al. | 564/339 |
| 3,669,965 | 6/1972 | White | 544/235 |
| 3,867,437 | 2/1975 | Fujimura et al. | 562/458 |
| 4,045,439 | 8/1977 | Preston et al. | 544/235 |
| 4,756,740 | 7/1988 | Labovitz et al. | 544/235 |
| 4,875,924 | 10/1989 | Mizutani | 544/235 |
| 4,956,460 | 9/1990 | Fusco et al. | 544/235 |

OTHER PUBLICATIONS

A. I. Meyers et al., "Oxazolines, XXII, Nucleophilic Aromatic Substitution on Aryl Oxazolines, An Efficient Approach to Unsymmetrically Substituted Biphenyls and o-Alkyl Benzoic Acids" in *J. Am. Chem. Soc.* (1975) 97(25):7383-7385.

Jerry March, "Reactions" in *Advanced Organic Chemistry 3rd. Ed.* (1985) pp. 587, published by John Wiley & Sons, New York.

Henry Feuer, "Activating Effects of the Nitro Group in Aromatic Substitutions" in *The Chemistry of the Nitro and Nitroso Groups* (1969) pp. 569-610, published by Interscience Publishers, New York.

A. I. Meyers et al., "Enantioselective Synthesis of Biphthyls via Nucleophilic Aromatic Substitution on Chiral Oxazolines" in *J. Am. Chem. Soc.* (1982) 104(3):879-881.

Primary Examiner—Mukund J. Shah
Assistant Examiner—E. Bernhardt
Attorney, Agent, or Firm—Cooley Godward Castro Huddleson & Tatum

[57] ABSTRACT

A method for the preparation of compounds of the formula

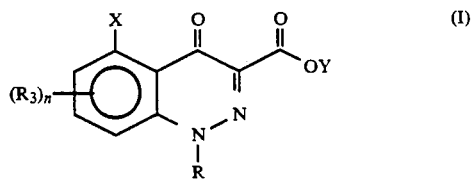

wherein X represents a group of the formula $OR_1$ or $NR_1R_2$, wherein $R_1$ and $R_2$ independently represent H or an organic group that forms a stable covalent bond with the N or O of said X; Y is H or an organic group that forms a stable ester with the adjacent COO group; R is an alkyl or aryl group optionally substituted with one or more stable organic substituents; each $R_3$ independently represents a stable organic group; and n is an integer from 0 to 3;

the method using new intermediates of the formula

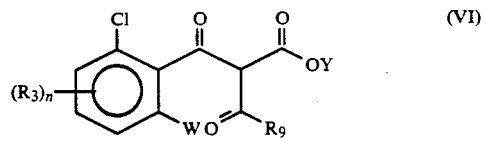

wherein $R_3$ and Y have the foregoing meanings;
W is either F or Cl;
and $R_9$ is a hydrocarbon such as a $C_1$-$C_4$ alkyl or alkenyl group.

19 Claims, No Drawings

METHOD FOR THE PREPARATION OF SUBSTITUTED 1,4-DIHYDRO-4-OXO-CINNOLINE-3-CARBOXYLIC ACID, ESTERS AND SALTS THEREOF, AND INTERMEDIATES USED IN THEIR PREPARATION

BACKGROUND OF THE INVENTION

1. Field Of The Invention

The present invention relates to a method for the preparation of certain substituted cinnoline derivatives, to new chemical intermediates used to prepare such cinnoline derivatives and to a method for the preparation of said intermediates. The substituted cinnoline derivatives have utility in regulating the fertility of certain plants.

2. Description Of The Background

Cross-breeding of plants has been commercially used for decades to alter the genetic make-up of plants. For successful cross-breeding, it is necessary to prevent the occurrence of self-pollination. In plants such as corn, self-pollination is prevented through mechanical means, as by removing the tassel which is the male portion of the plant and thus its pollen source. However, in other plants, such as wheat, the physiology of the plant prevents mechanical means from being successfully used to prevent self-pollination. In such plants, the male part is inaccessibly located in close proximity to the female part, making the use of mechanical intervention impractical.

Prevention of self-pollination in plants such as wheat requires a chemical means to suppress the formation of active pollen. Certain chemical pollen suppressants have already been suggested in the art, as discussed, for example, in U.S. Pat. Nos. 4,561,881, 4,604,134, 4,729,782, and 4,756,740 and the references discussed therein. Such pollen suppressants chemically inhibit the formation of pollen or induce the plant to produce non-functioning pollen. More recently, it has been discovered that certain 5-oxy or 5-amino substituted 1,4-dihydro-4-oxo-cinnoline-3-carboxylic acids and esters and salts thereof have superior pollen suppression activity, as disclosed in U.S. patent application Ser. No. 243,895, filed Sep. 13, 1988. The chemical pollen suppressants of that application are species of compounds having the formula:

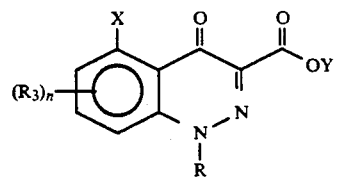

wherein X represents a group of the formula $OR_1$ or $NR_1R_2$ wherein $R_1$ represents a $C_1$–$C_4$ alkyl (optionally substituted with a $C_1$–$C_4$ alkoxy group, 1 to 3 halogen atoms, or a carboxy or $C_1$–$C_4$ alkoxycarbonyl group), a $C_2$–$C_4$ alkenyl (optionally substituted with 1 to 3 halogen atoms), or a $C_2$–$C_4$ alkynyl group and $R_2$ represents H or $CH_3$, with the proviso that when $R_1$ is $CH_3$, $R_2$ is $CH_3$;

Y is hydrogen, $C_1$–$C_{22}$ linear alkyl or alkenyl containing up to four carbon-carbon double bonds, $C_3$–$C_6$ branched alkyl or alkenyl, $C_1$–$C_4$ alkoxyalkyl, cyclohexylmethyl, halogenated $C_1$–$C_4$ alkyl, phenyl, benzyl, —$(CH_2CH_2O)_mCH_2CH_3$ in which m is an integer from 1 to 5, or —$CH(CH_2OR_4)CH_2OR_5$ or —$CH_2CHOR_4CH_2OR_5$ in which either $R_4$ or $R_5$ but not both represent a $C_1$–$C_{22}$ linear alkyl- or alkenylcarbonyl group containing up to four carbon-carbon double bonds and the other of $R_4$ or $R_5$ is H; and R represents $C_1$–$C_4$ alkyl, phenyl, naphthyl, or phenyl or naphthyl substituted with one to three substituents selected from the group consisting of halogen, $CONH_2$, $C_1$–$C_4$ alkyl or haloalkyl, $C_1$–$C_4$ alkoxy or haloalkoxy, and cyano;

and salts thereof.

Unfortunately, the chemical pollen suppressants disclosed in the aforementioned application are somewhat difficult to prepare and require the use of expensive starting materials. In particular, the compounds disclosed in that application have typically been synthesized by reacting difluorobenzoyl chloride and derivatives thereof with acetonides. The difluorobenzoyl chloride and its derivatives have the formula:

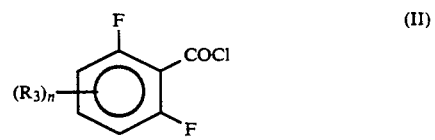

wherein $R_3$ and n have the previously defined meanings, and the acetonides have the formula:

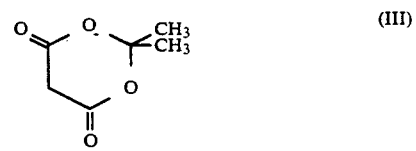

Fluorinated compounds such as those of the foregoing Formula II are very expensive raw materials as are the acetonides of Formula III and the solvents (such as DMAP) in which these compounds are normally reacted. Thus, while synthesis of compounds of Formula I was possible in the laboratory, commerical production in large scale was economically unfeasible.

It is apparent that a need exists for a procedure for synthesizing compounds of Formula I which does not require the use of expensive or difficult-to-obtain starting materials and solvents. Heretofore, that need has not been satisfied by any of the known synthesis routes for manufacturing such compounds.

SUMMARY OF THE INVENTION

Surprisingly, there has now been discovered an efficacious method for the preparation of the substituted 1,4-dihydro-4-oxo-cinnoline-3-carboxylic acids and esters and salts thereof, especially those of Formula I, which avoids the need for expensive or unavailable raw materials and the need for extreme reaction conditions. The new method uses less-expensive, readily available starting materials to produce a new chemical intermediate which is unknown in the art and which has never been used to synthesize these compounds.

In accordance with the present invention certain new intermediates are first synthesized from readily available, relatively inexpensive starting materials by a process which comprises reacting a chlorobenzoyl compound (preferably a benzoyl chloride) or a derivative thereof with a ketocarboxylate, wherein the chlorobenzoyl compound and derivatives thereof have the following formula:

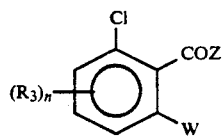

wherein each $R_3$ is a stable organic group which can be the same or different and n is an integer from 0 to 3;

W is either F or Cl; and

Z is a leaving group selected from the group consisting of H, $NR_6R_7$, $OR_8$, and halogen, wherein $R_6$ and $R_7$ are independently selected from H and organic groups that form stable amides with the adjacent CON functional group and $R_8$ is an organic group that forms a stable ester with the adjacent COO functional group.

The ketocarboxylate which is reacted with the dichlorobenzoyl compound of formula IV has the following formula:

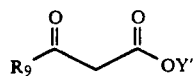

wherein Y' is a stable organic group that forms an ester with the adjacent COO group of the formula, preferably a group selected from the previous definition of Y, and $R_9$ is a hydrocarbon group, especially one in which an alkyl group is present adjacent to the β-keto group, with $R_9$ preferably being entirely a short-chain hydrocarbon, such as an alkyl or alkenyl group having from 1 to 4 carbon atoms, more preferably a methyl group.

Reaction of the dichlorobenzoyl compound of formula IV with the ketocarboxylate of formula V results in the formation of a 2,6-dichlorobenzoylketocarboxylate or trione having the following formula:

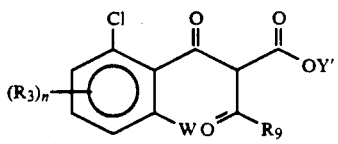

wherein $R_3$, $R_9$, W, Y', and n have the previously defined meanings.

Through further chemical conversion, using procedures known in the art, the compounds of Formula VI may be readily transformed into the desired compounds of Formula I and related compounds. The compounds of Formula VI are new chemical entities that provide a new synthetic route to substituted cinnolines as described herein.

DESCRIPTION OF SPECIFIC EMBODIMENTS

The present invention provides a novel process for the preparation of substituted 1,4-dihydro-4-oxocinnoline-3-carboxylic acids, esters, and salts thereof in which an oxy or amino substituent is present at position 5 of the derivatized cinnoline ring. A key step in the process is the reaction of a chlorobenzoyl compound with a keto carboxylate. The resulting triones not only represents a new synthetic route to cinnolines, they are novel compounds in and of themselves. Thus, the present invention provides a process for the preparation of certain chemical pollen suppressants and other compounds of the formula:

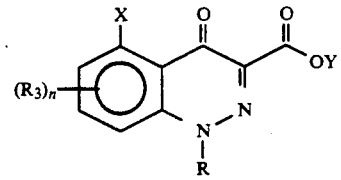

wherein X represents a group of the formula $OR_1$ or $NR_1R_2$ wherein $R_1$ represents a $C_1$-$C_4$ alkyl (optionally substituted with a $C_1$-$C_4$ alkoxy group, 1 to 3 halogen atoms, or a carboxy or $C_1$-$C_4$ alkoxycarbonyl group), a $C_2$-$C_4$ alkenyl (optionally substituted with 1 to 3 halogen atoms), or a $C_2$-$C_4$ alkynyl group and $R_2$ represents H or $CH_3$, with the proviso that when $R_1$ is $CH_3$, $R_2$ is $CH_3$;

Y is hydrogen, $C_1$-$C_{22}$ linear alkyl or alkenyl containing up to four carbon-carbon double bonds, $C_3$-$C_6$ branched alkyl or alkenyl, $C_1$-$C_4$ alkoxyalkyl, cyclohexylmethyl, halogenated $C_1$-$C_4$ alkyl, phenyl, benzyl, -$(CH_2CH_2O)_mCH_2CH_3$ in which m is an integer from 1 to 5, or —$H(CH_2OR_4)CH_2OR_5$ or —$CH_2CHOR_4CH_2OR_5$ in which either $R_4$ or $R_5$ but not both represent a $C_1$-$C_{22}$ linear alkyl- or alkenylcarbonyl group containing up to four carbon-carbon double bonds and the other of $R_4$ or $R_5$ is H;

R represents $C_1$-$C_4$ alkyl, phenyl, naphthyl, or phenyl or naphthyl substituted with one to three substituents selected from the group consisting of halogen, $CONH_2$, $C_1$-$C_4$ alkyl or haloalkyl, $C_1$-$C_4$ alkoxy or haloalkoxy, and cyano;

each $R_3$ is a stable organic group which can be the same or different and is preferably $C_1$-$C_4$ alkyl or haloalkyl, $C_1$-$C_4$ alkoxy or haloalkoxy, $C_1$-$C_4$ alkanoyl, cyano, nitro, hydroxy, and most preferably hydrogen, and n is an integer from 0 to 3;

and salts thereof, as well as related cinnolines with different substituents. The substituents listed in the previous sentence are desirable because the indicated compounds are pollen suppressants having especially good properties for field use. However, the method of synthesis is not limited to these specific compounds, which should be considered exemplary of the types of cinnolines that can be prepared by the new synthetic route described herein.

The substituents that are in locations where a reaction is not taking place (for any particular step of the reaction scheme) can generally be any stable organic substituent. By "stable organic substituent" is meant any carbon- or heteroatom-containing substituent found in organic chemistry that will not interfere with that particular step of the reaction scheme. There is no particular limitation of the size of the substituent, although extremely large substituents may result in compounds that are difficult to dissolve or otherwise manipulate. Substituents therefore generally have 20 or fewer, preferably 15 or fewer, more preferably 10 or fewer atoms (other than hydrogens), except where noted. Likewise, there are no limitations on functional groups that can be present in the substituents, except for those (as will be recognized by those skilled in the art of organic synthesis) that interfer with completion of the indicated reactions. However, even reactive substituents can be present in some of the claimed new compounds that can function as intermediates in the overall synthesis, since such reactive groups can be protected (such as by acetylation of an amine) before the compounds undergo the indicated reactions. Examples of preferred substituents are given throughout this specification, and particular limitations on the structure of substituents are given in cases where the substituent participates in a reaction step, such as for leaving groups in reactions.

GENERAL SYNTHESIS ROUTE

The present invention provides a method for the preparation of substituted cinnolines, including the substituted cinnoline derivatives of Formula I, through the following reaction sequence. In this reaction scheme, substituents not involved in the actual reaction being shown have the meanings previously indicated.

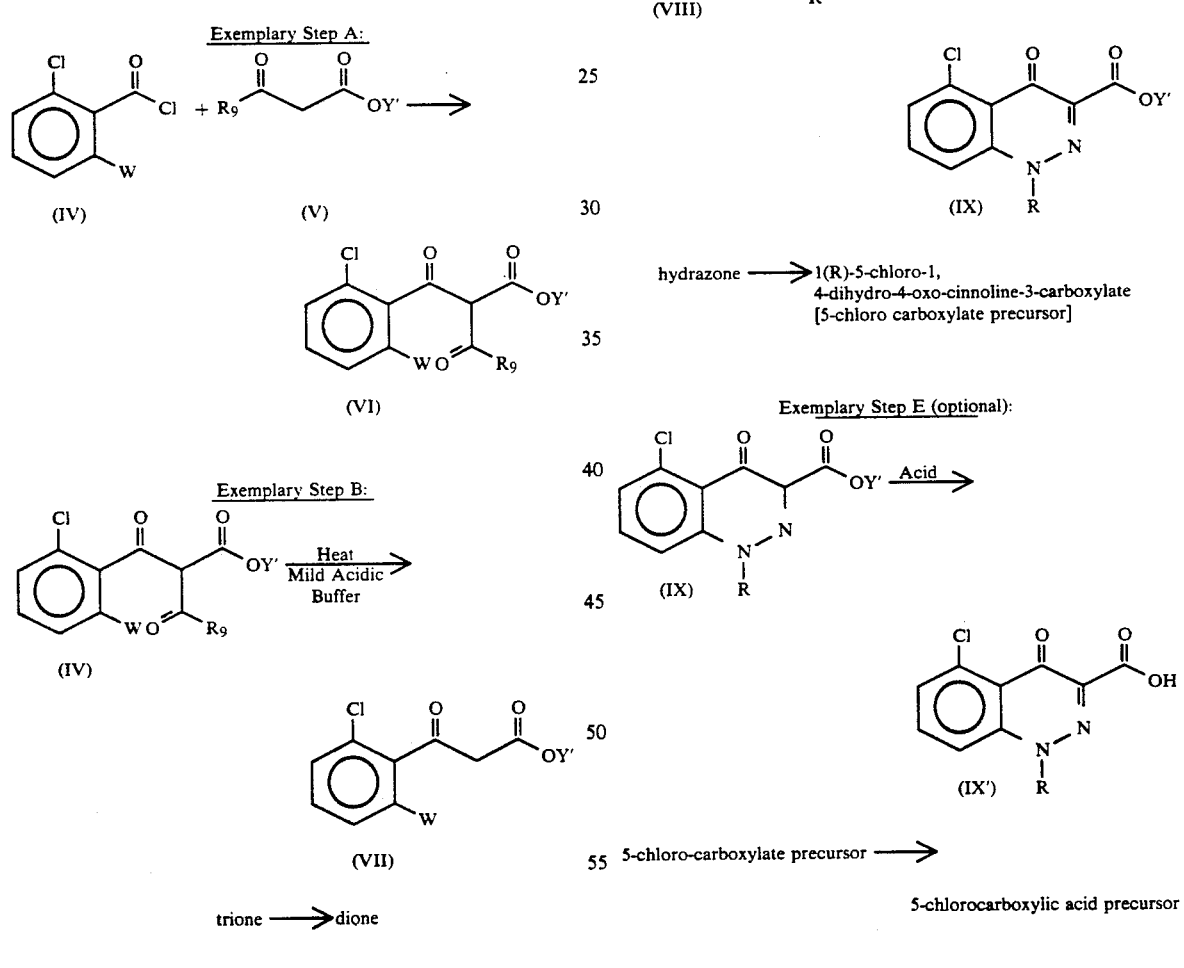

trione ⟶ dione

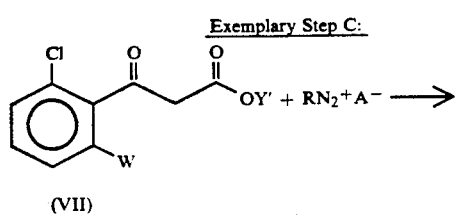

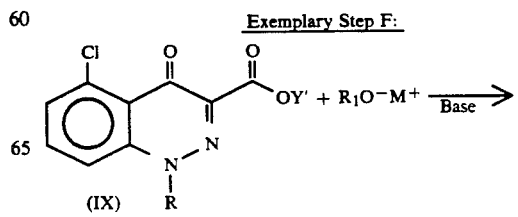

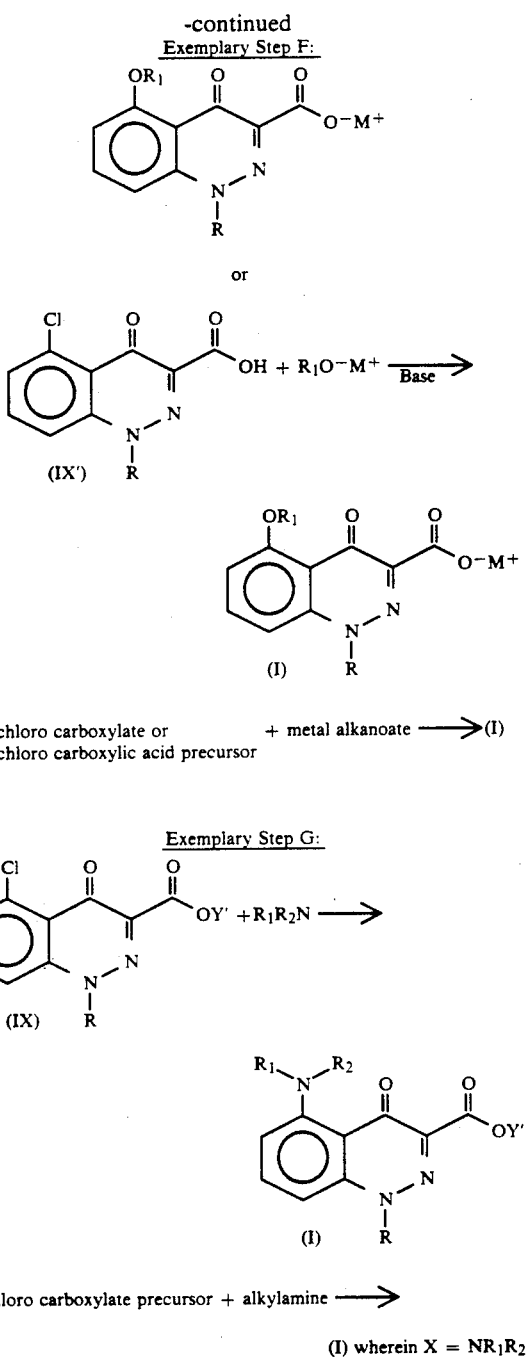

Exemplary Step F:

5-chloro carboxylate or 5-chloro carboxylic acid precursor + metal alkanoate ⟶ (I)

Exemplary Step G:

5-chloro carboxylate precursor + alkylamine ⟶

(I) wherein X = NR₁R₂

Steps A and B above are new synthesis procedures which are not found in the prior art in the synthesis of compounds of Formula I, whereas Steps C through G are generally well-known procedures which have been used previously in the art in the synthesis of compounds of Formula I.

Step A not only is a new reaction, but the 2(2′,6′-dihalobenzoyl)-3-ketocarboxylate, or trione, product of that reaction is a new chemical entity.

Likewise, the reaction of Step B also is not known in the production of substituted cinnolines, and in combination with Step A affords a method for obtaining a 2,6-dihalobenzoyl carboxylate which previously could only be obtained through use of more expensive starting materials and extreme laboratory conditions.

Steps B and C can be combined by reacting the trione directly with the diazonium salt (Japp-Klingman reaction).

SPECIFIC REACTION CONDITIONS

Although, in general, the reaction conditions used in the practice of the method of the present invention are not critical, certain specific conditions yield preferred results in terms of the yield or purity of the desired products, their rate of formation, or other considerations. On that basis, the preferred reaction conditions for each of the steps are set forth below.

Step A: Formation of 2,6-dichlorobenzoyl ketocarboxylate—Trione

Generally from about 1 to about 3 moles of the ketocarboxylate is employed per mole of 2,6-dichlorobenzoyl chloride or derivatives thereof. Preferably an aprotic solvent is used, most preferably one selected from the group consisting of toluene/methylcyanide (at a usual volume ratio of about 2:1), methylcyanide, tetrahydofuran (THF), or THF/methylcyanide (1:2). The reaction temperature is generally from about 60, to about 90° C., and the reaction takes place in the presence of a catalytic amount of a base such as pyridine and magnesium chloride and generally proceeds for about 3 to about 8 hours.

Step B: Formation of 2,6-dichlorobenzoyl carboxylate—Dione

The 2,6-dichlorobenzoyl ketocarboxylate is converted to the corresponding 2,6-dichlorobenzoyl carboxylate by heating the starting compound in an organic solvent at a temperature from about 50 to about 100° C. for about 6 to about 36 hours. Preferably, the organic solvent is an alcohol such as methanol. The conversion reaction takes place most readily if the reaction mixture is buffered, preferably at a pH from about 4 to about 7. The preferred buffer is potassium hydroxide/acetic acid, although other buffers such as potassium phosphate can also be used. Preferably the ratio of the molarity of the buffer to the molarity of the starting carboxylate is from about 10:1 to about 2:1. After completion of the reaction, an appropriate organic solvent, such as methylene chloride, can be used as a vehicle for the entire reaction mixture, which then can be suitably washed with water to remove the buffer, followed by drying of the organic layer and vacuum removal of the solvent to recover the desired product.

Step C: Formation of Hydrazone

A diazonium salt is first prepared by means known in the art, typically by reacting an amine of the formula RNH₂ with sodium nitrite by first adding the amine to concentrated acid, such as hydrochloric, to form an amine salt which subsequently is combined with an aqueous solution of sodium nitrate. The resultant diazonium salt is then added to the 2,6-dichlorobenzoyl carboxylate in a suitable organic solvent, such as methanol, containing sodium acetate. The desired hydrazone precipitates from solution and can then be collected by filtration, followed by washing with water and vacuum drying.

Step D: Formation of 1(R)-5-chloro-1,4-dihydro-4-oxo-cinnoline-3-carboxylate—5-chloro carboxylate precursor About 1 to about 2 equivalents of a base such as potassium carbonate per mole of hydrazone is combined in an anhydrous solvent, such as dimethylformamide, along with a catalytic amount of a crown ether, such as 18-crown-6. The resulting mixture is then warmed to a temperature of about 110 to about 150° C. for about ½ to about 4 hours, under a nitrogen atmosphere. After cooling, the reaction mixture is poured into water with stirring, and the desired 5-chloro carboxylate precursor removed.

Step E: Formation of 1(R)-5-chloro-1,4-dihydro-4-oxo-cinnoline-3-carboxylic acid—5-chloro carboxylic acid precursor The 5-chloro carboxylate precursor is placed in an appropriate solvent such as p-dioxane which is then acidified with a strong acid such as hydrochloric acid. The mixture is then refluxed for about 4 hours to about 12 hours to complete the saponification reaction, after which the mixture is cooled and poured into water and the 5-chloro carboxylic acid precursor precipitate filtered and dried under vacuum.

Step F: Formation of 1(R)-5-(oxy substituted)-1,4-dihydro-4-oxo-cinnoline-3-carboxylic acid Either the 5-chloro carboxylate precursor or the 5-chloro carboxylic acid precursor is placed in a suitable organic solvent such as tetrahydrofuran (THF), dimethyl formamide (DMF), p-dioxane, or methanol, to which a base, such as potassium hydroxide, is added, along with an alcohol having the formula $R_1OH$, wherein $R_1$ has the previously defined meaning to form the corresponding potassium alkoxide. The resultant mixture is refluxed for about 8 to about 16 hours, then cooled and acidified and the product recovered as the salt or, if acidified before recovery, as the free acid, by filtration and drying over vacuum.

Step G: Formation of 1(R)-5-(amino substituted)-1,4-dihydro-4-oxo-cinnoline-3-carboxylic acid The desired alkylamine or dialkylamine $R_1R_2N$ wherein $R_1$ and $R_2$ have the previously defined meanings (10 equivalents) is added to a solution or suspension of the starting 5-chloro-4-oxo-cinnoline-3-carboxylic acid precursor in aqueous dioxane or another suitable solvent. The mixture is refluxed overnight. The reaction is followed by HPLC, and, upon completion, the mixture is diluted with two volumes of cold water or another miscible liquid in which the product is less soluble. After the pH is adjusted to the isoelectric point, the product precipitates and is collected by filtration, washing with water, and drying.

DESCRIPTION OF PREFERRED CONSTITUENTS

In one preferred embodiment of the invention, $-CO_2Y$ is a carboxy group or a salt thereof. When $-CO_2Y$ is a salt of a carboxy group, the cation can be an alkali metal ion, alkaline earth metal ion, or transition metal ion. The cation can also be an ammonium or substituted ammonium ion. Representative alkali metal ions, which are preferred, include lithium, sodium, and potassium ions; representative alkaline earth metal ions include magnesium, calcium, and barium ions; representative transition metal ions include zinc, manganese, iron, titanium, and molybdenum ions; and representative ammonium ions, which are also preferred, include the ammonium ion itself and alkyl-substituted ammonium ions (especially alkanol-substituted ammonium ions).

Preferred substituents at other positions are those in which R represents a phenyl group with zero to three substituents selected from the group consisting of halogen, $-CONH_2$, $C_1-C_4$ alkyl or haloalkyl (especially trihalomethyl), $C_1-C_4$ alkoxy or haloalkoxy, and cyano ("haloalkyl" and similar terms referring to halogenated molecules include both mono- and polyhalogenated compounds); more preferably the phenyl is substituted with one of said substituents; even more preferably with one halogen atom; and most preferably with chlorine in the para position; Y is H, Na, K, $C_1-C_{22}$ linear alkyl or alkenyl containing up to four carbon-carbon double bonds, $C_1-C_4$ alkoxyalkyl, cyclohexylmethyl, halogenated $C_1-C_4$ alkyl, phenyl, benzyl, $-(CH_2CH_2O)_mCH_2CH_3$ in which m is an integer from 1 to 5, or $-CH(CH_2OR_4)CH_2OR_5$ or $-CH_2CHOR_4CH_2OR_5$ in which either $R_4$ or $R_5$ but not both represents a $C_1-C_{22}$ linear alkyl or alkenyl group containing up to four carbon-carbon double bonds (the other of $R_4$ or $R_5$ representing hydrogen); and X represents a group of the formula $OR_1$ or $NR_1R_2$ wherein the $R_1$ represents a $C_1-C_4$ alkyl (optionally substituted with a $C_1-C_4$ alkoxy group, 1 to 3 halogen atoms, or a carboxy or $C_1-C_4$ alkylcarbonyl group), alkenyl, or alkynyl group and $R_2$ represents H or $CH_3$, with the proviso that when $R_1$ is $CH_3$, $R_2$ is $CH_3$.

Among the preferred esters of the carboxylic acid group at position 3 of the cinnoline ring are esters formed from fatty alcohols or from fatty acid monoglycerides. Examples of fatty alcohols include arachidyl, cetyl, decanol, lauryl, linolenyl, linoleyl, and oleyl alcohols. Examples of fatty acids include the fatty acids corresponding to these fatty alcohols. The fatty acids are typically reacted first with glycerin to form monoglycerides (the reaction occurring at either the 1 or the 2 position), with the resulting monoglyceride being reacted at either of the free hydroxyl groups to form the final ester. Other preferred esters include those prepared from linear and branched $C_1-C_6$ alkanols.

Another grouping of preferred substituents includes those in which the substituents on a phenyl group in the R position are selected from the group consisting of 3',4'-dichloro, 3',4'-difluoro, 4'-trifluoromethoxy, 4'-chloro, 4'-methyl, 4'-methoxy, 4'-cyano, 4'-trifluoromethyl, 4'-iodo, 4'-fluoro, 4'-bromo, 4'-acetyl, 3'-fluoro, 3'-chloro, 3'-trifluoromethyl, 2'-fluoro, 2'-chloro, and 2'-trifluoromethyl. At the Y location, tetrabutyl ammonium and tetramethyl ammonium salts are especially preferred along with ammonium salts containing alkanol substituents in place of alkyl substituents. Preferred $-CO_2Y$ groups are acids and acid salts, although esters as described above are nearly as preferred. Among acid salts, quaternary ammonium salts are preferred, as they enhance stability. The $OR_1$ substituent is preferably $-OMe$, $-OEt$, $-OnPr$, $-OiPr$, $-OCH_2CH=CH_2$, $-OiBu$, $-OCH_2CH_2OCH_3$, $-OCH_2CH_2OCH_2CH_3$, or $-NMe_2$.

Certain combinations of substituents are especially preferred. One preferred group occurs when R is phenyl or phenyl mono-substituted with a halogen, trihalomethyl, or cyano group at position 4' or a halogen at position 2'; Y is —H, —Na, or K; and OR$_1$ represents —OMe, —OEt, —OnPR, —OiPr, —OCH$_2$CH=CH$_2$, —OiBu, —NMe$_2$, —OCH$_2$CH$_2$OCH$_3$, or —OCH$_2$CH$_2$OCH$_2$CH$_3$.

Also included within the scope of the invention is the formation of agronomically acceptable acid addition salts of compounds having the general Formula I.. Typical acid addition salts are formed with strong acids such as hydrochloric, hydrobromic, and sulfuric acids. Salts of acidic or basic functional groups, such as the —CO$_2$Y or —X groups, may also be formed in this invention. Throughout this application, agronomically acceptable salt means that the salt is not substantially more toxic to the plant or to the consumer of the plant than the parent compound from which the salt is formed.

Typical compounds produced by the process of the invention include the following:

1-phenyl-1,4-dihydro-4-oxo-5-methoxycinnoline-3-carboxylic acid 1-(4'-chlorophenyl)-1,4-dihydro-4-oxo-5-(1'''-carboxyethoxy)cinnoline-3-carboxylic acid 1-(4'-fluorophenyl)-1,4-dihydro-4-oxo-5-ethoxycinnoline-3-carboxylic acid 1-phenyl-1,4-dihydro-4-oxo-5-(2''-methoxyethoxy)cinnoline-3-carboxylic acid 1-(4'-chlorophenyl)-1,4-dihydro-4-oxo-5-n-propyloxycinnoline-3-carboxylic acid 1-(4'-trifluoromethyl)-1,4-dihydro-4-oxo-5-dimethylaminocinnoline-3-carboxylic acid 1-(3',4'-dichlorophenyl)-1,4-dihydro-4-oxo-5-methoxycinnoline-3-carboxylic acid 1-(4'-cyanophenyl)-1,4-dihydro-4-oxo-5-(prop-2''-enoxy)cinnoline-3-carboxylic acid 1-(4'-fluorophenyl)-1,4-dihydro-4-oxo-5-i-butoxycinnoline-3-carboxylic acid 1-(3'-chlorophenyl)-1,4-dihydro-4-oxo-5-dimethylaminocinnoline-3-carboxylic acid 1-(4'-trifluoromethylphenyl)-1,4-dihydro-4-oxo-5-methoxycinnoline-3-carboxylic acid as well as the ammonium, sodium, potassium, and lithium carboxylate salts of each of the above compounds and the acid addition salts of each of the above listed compounds. By carboxylate salt is meant a salt of a carboxylic acid group at C-3. By acid addition salt is meant a salt formed by the protonation of a ring or side chain nitrogen.

Aromatic substituents, R$_2$, may also be present. Groups that would interfere with the ring-forming reaction or other reactions may be present in protected form (e.g., an acylamino group that may later be converted into an amine), or they may be added later (e.g., by halogenation of the phenyl rings), or they may be prepared by conversion of a suitable group present during synthesis (e.g., the above-mentioned amino group may be diazotized and converted into many different functional groups).

The above-indicated 3-carboxycinnolines can then be converted into other compounds by known methods. For example, the carboxylic acid group can be converted into a carboxylate salt or a protected amino group can be deprotected, diazotized, and converted into a different functional group by simple synthetic manipulations within the ordinary skill of a synthetic organic chemist.

Having now generally described this invention, the same will be better understood by reference to certain specific examples which are included herein for purposes of illustration only and are not intended to be limiting of the invention or any embodiment thereof unless so specified.

EXAMPLES I(a)–I(i)

Preparation of Methyl 2,6-Dichlorobenzoylacetoacetate

I(a)

To a stirred slurry of 190 g (2 moles) of magnesium chloride in 1 liter of acetonitrile is added 232 g (2 moles) of methyl acetoacetate, the reaction is cooled to 0° C., and there is then added 324 ml (4 moles) of pyridine dropwise such that the temperature does not exceed 5° C.

After the mixture is stirred at room temperature for 30 minutes, 419 g (2 moles) of 2,6-dichlorobenzoyl chloride in 1 liter of toluene is added and the reaction heated to reflux for 4 hours (85°–90° C.).

The reaction is then cooled to 0° C., and there is slowly added 133 ml (2.4 moles) of concentrated sulfuric acid. The mixture is extracted with water/ methylene chloride to separate the aqueous layers (pH=1), washed with water once (pH=4), dried and the solvent evaporated in vacuo to give 535 g (92.5%) of the crude trione.

I(b)–I(i)

Following the general procedure of Example I(a), Examples I(b)–I(i) are prepared using different solvents and using principal reaction conditions of 65°–85° C., for 3 to 8 hours. The amount of acetoacetate employed is set forth in Table 1, along with the purity and yield of the resulting product where available. In some cases (indicated by a "-" at the appropriate location in the following Tables), data was not obtained on purity and yield.

TABLE 1

Summary Of Reaction Conditions And Results For Preparation Of Methyl Dichlorobenzoylacetoacetates

| RXN | Solvent | [Acetoacetate]$^1$ | (%) Purity | (%) Yield |
|---|---|---|---|---|
| I(b) | p-Dioxane | 0.25 | — | — |
| I(c) | Monoglyme | 0.25 | — | — |
| I(d) | Diglyme | 0.25 | — | — |
| I(e) | C$_6$H$_5$CH$_3$/CH$_3$CN (2:1) | 0.50 | 80 | 87 |
| I(f) | CH$_3$CN | 0.25 | 78 | 87 |
| I(g) | THF/CH$_3$CN (1:2) | 0.50 | 68 | 33 |
| I(h) | THF | 0.50 | 91 | 93 |
| I(i) | THF | 1.67 | 85 | 88 |

$^1$Moles acetoacetate per liter of solvent

EXAMPLES II(a)–II(h)

Preparation of Methyl 2,6-Dichlorobenzoylacetate

II(a)

There is prepared 1.85 M KOAc/MeOH/AcOH buffer by dissolving 544 g (5.55 moles) of potassium acetate in 2.2 l of methanol and adding 570 ml of acetic acid to reach pH=6.5 and a final volume of 3.0 l.

The above buffer is added to the crude trione of Example I (1.85 moles) and heated to a reflux for 16-20 hours (65°–70° C.). The reaction can be monitored by HPLC to assure completion.

After being cooled to room temperature, the mixture is taken up in methylene chloride and washed with water to remove buffer (pH=5–6). The organic layer is dried and solvent is removed in vacuo to afford 365 g (80%) of the beta-keto ester with a purity of 90%.

II(b)–II(h)

Following the general procedure of Example II(a), Examples II(b)–II(h) are performed using different reagents and pH conditions, using principal reaction conditions of 50°–65° C., for 16 to 24 hours. The nature and amount of reagent employed and pH are set forth in Table 2, along with the purity and yield of the resulting products where available.

TABLE 2

Summary Of Reaction Conditions And Results For Preparation Of Methyl Dichlorobenzoylacetates

| RXN | Reagents | [Reagent] | pH | (%) Purity | (%) Yield |
|---|---|---|---|---|---|
| II(b) | $Zn(OAc)_2 \cdot 2H_2O$ | 1.50 | 5.8 | — | — |
| II(c) | $Zn(OAc)_2 \cdot 2H_2O$ | 0.01 | 7.3 | — | — |
| II(d) | AcOH | 10.00 | 0.8 | — | — |
| II(e) | $ZnCl_2$ | 1.25 | 4.5 | 82 | 46 |
| II(f) | KOAc/AcOH | 1.58 | 7.5 | 74 | 40 |
| II(g) | KOAc/AcOH | 1.41 | 6.4 | 86 | 46 |
| II(h) | KOAc/AcOH | 1.31 | 5.3 | 83 | 54 |

EXAMPLES III(a)–III(f)

Preparation of 1-(4′-chlorophenyl)-5-methoxyethoxy-1,4-dihydro-4-oxo-cinnoline-3-carboxylic acid III(a)

1. Preparation of methyl 3-(2,6-dichlorophenyl)-2-3-dioxopropionate-2-(4-chlorophenyl) hydrazone To 13.4 g (0.105 mole) of 4-chloroaniline in 80 ml of methanol was added 33.4 ml (4.0 eq.) of concentrated HCl with ice water cooling. There was then added at 0°–5° C. 7.2 g (0.105 mole) of $NaNO_2$ in 20 ml of $H_2O$ with vigorous stirring. The resulting solution of diazonium salt is then added with continued stirring at 5°–10° C. to a solution of methyl 2,6-dichlorobenzoylacetate (24.7 g) in 150 ml of MeOH containing 29.7 g (3 eq.) of potassium acetate. The resulting precipitate is collected by filtration, washed with $H_2O$, and dried over vacuum at 50° C. (28.6 g, 74%).

2. Preparation of methyl 1-(4′-chlorophenyl)-5-chloro-1,4-dihydro-4-oxo-cinnoline-3-carboxylate To 12 g (31 mmole) of the above hydrazone (from step 1) in 150 ml of dry dimethyl formamide are added 4.3 g (1.0 eq.) of $K_2CO_3$ and a catalytic amount of 18-crown-6 at room temperature. The mixture is warmed to 130° C. for 1 hour, under a nitrogen atmosphere. After cooling, the mixture is poured into water with stirring. 10 g (92.4%) of crude product is made.

3. Preparation of 1-(4′-chlorophenyl)-5-chloro-1,4-dihydro-4-oxo-cinnoline-3-carboxylic acid To 10 g (28.6 mmole) of the above methyl ester (from step 2) in 150 ml of p-dioxane there is added 10 ml (4 eq.) of concentrated HCl with stirring under a nitrogen atmosphere. The mixture is heated up and refluxed for 5 hours. After cooling, the mixture is poured into water with stirring. Free acid is collected by filtration and dried over vacuum at 50° C. (9.5 g, 99%).

4. Preparation of 1-(4′-chlorophenyl)-5-methoxyethoxy-1,4-dihydro-cinnoline-4-oxo-3-carboxylic acid To 0.5 g (1.5 mmole) of the above free acid (from step.3) in 20 ml of THF there is added a mixture of 0.8 g (8 eq) of KOH in 5 ml of 2-methoxy-ethanol at room temperature. The entire mixture is refluxed for 5 hours, cooled, and acidified with 1 N HCl. The product is filtrated and dried over vacuum at 50° C. (0.52 g, 93%).

III(b)–III(f)

Following the general procedure of Example III(a), Examples III(b)–III(f) are performed using different solvents, reaction temperatures, and reaction times, all as set forth in Table 3. Also set forth in that table are the purity and yields obtained in each instance where available.

TABLE 3

Summary of Reaction Conditions And Results For Making 1-(4′-chlorophenyl)-5-methoxyethoxy 1,4-dihydro-4-oxo-cinnoline-3-carboxylic Acid

| Eq. of KOH | (°C.) rxn Temp. | Solvent | (hrs.) rxn Time | (%) Purity | (%) Yield |
|---|---|---|---|---|---|
| III(b) | 75 | p-dioxane | 2 | 95 | 89 |
| III(c) | 85 | p-dioxane | 3 | 89 | 90 |
| III(d) | 100 | p-dioxane | 15 | 96 | 92 |
| III(e) | 100 | THF | 4 | 96 | 93 |
| III(f) | room | DMF | 15 | — | — |

EXAMPLES IV(a)–IV(f)

Preparation of 1-(4′-fluorophenyl)-5-methoxy-1,4-dihydro-4-oxo-cinnoline-3-carboxylic acid IV(a)

1. Preparation of methyl 3-(2,6-dichlorophenyl)-3-oxo-propionate-2-(4′-fluorophenyl) hydrazone To 10.55 g (95 mmole) of 4-fluoroaniline in 80 ml of methanol there is added 33.3 ml (4 eq.) of concentrated HCl with ice water cooling. There is then added at 0°–5° C., 6.5 g (95 mmoles) of $NaNO_2$ in 20 ml of $H_2O$, while stirring is vigorously maintained. The resulting solution of diazonium salt is then added with stirring at 5°–10° C. to a solution of methyl 2,6-dichlorobenzoylacetate (24.7 g, 90 mmole) in 150 ml of MeOH containing 29.2 g (3.0 eq) of potassium acetate. The resulting precipitate is collected by filtration, washed with $H_2O$, and dried over vacuum at 50° C. (21.2 g, 57%).

2. Preparation of methyl 1-(4′-fluorophenyl)-5-chloro-1,4-dihydro-4-oxo-cinnoline-3-carboxylate To the above 21.2 g (57.4 mmole) of hydrazone in 180 ml of dry DMF there is added 7.94 g (1 eq) of $K_2CO_3$ and a catalytic amount of 18-crown-6 at room temperature. The mixture was warmed up to 130° C. for 1 hour under $N_2$ atmosphere. After cooling, the mixture is poured into water with stirring. The product is collected by filtration, washed with $H_2O$, and dried over vacuum at 50° C. (18.5 g, 97%).

3. Preparation of 1-(4′-fluorophenyl)-5-methoxy-1,4-dihydro-cinnoline-4-oxo-3-carboxylic acid To 1.0 g (3.0 mmole) of the above methyl ester (from step 2) in 40 ml of THF there are added 2.0 g (10 eq. 85%) of KOH in 20 ml of MeOH and catalytic amount of 18-crown-6 at room temperature. The mixture is refluxed overnight. 0.9 g (92%) of crude product is prepared after acidifying with 1 N HCl.

IV(b)–IV(f)

Following the general procedure of Example IV(a), Examples IV(b)–IV(f) were performed, using different solvents, various proportions of potassium hydroxide and either the methyl ester, as in Example IV(a), or the free acid as the starting material, all as set forth in Table 4, along with the purity and yields of the product where available.

TABLE 4

Summary Of Reaction Conditions And Results For Making 1-(4'-Fluorophenyl)-5-methoxy-1,4-dihydro-4-oxo-cinnoline-3-carboxylic Acid

| RXN | Reactant | Eq. of KOH | Solvent | (%) Purity | (%) Yield |
|---|---|---|---|---|---|
| IV(b) | Ester | 15.0 | MeOH | 58 | — |
| IV(c) | Acid | 13.5 | p-dioxane | 50 | — |
| IV(d) | Ester | 15.0 | p-dioxane | — | — |
| IV(e) | Acid | 5.0 | THF (18-crown-6) | 86 | 98 |
| IV(f) | Acid | 8.0 | THF (18-crown-6) | 97 | 96 |

EXAMPLE V

Preparation of 1-(4'chlorophenyl)-5-methoxyethoxy-1,4-dihydro-4-oxocinnoline-3-carboxylic acid 1. Preparation of methyl 2,6-dichlorobenzoylacetoacetate A slurry of anhydrous magnesium chloride (571 g, 6.0 moles) and methyl acetoacetate (697 g, 6.0 moles) in 3 l of acetonitrile was stirred in an ice-salt bath as 972 ml of pyridine (12 moles) was added at such a rate that the temperature did not exceed 5° C. (addition time 2 hrs.). The cooling bath was removed and toluene (500 ml) was added at once followed by the addition of a solution of 1255 g of 2,6-dichlorobenzoyl chloride (6.0 moles) in 1.5 l of toluene over one hour (final temperature 25° C.). The reaction was heated at reflux for 5 hours, and then allowed to cool over 14 hours to room temperature. The reaction was cooled in an ice bath to 0° C., and 400 ml of concentrated sulfuric acid (7.3 moles) was then added to the reaction mixture at a rate to maintain a temperature below 15° C., followed by 1.5 l of water. The mixture was stirred for 30 min. The organic layer was isolated and washed with 3 l of water. The acidic aqueous washes were back-extracted with 1 l of toluene. The product was extracted from the combined organic layers with an aqueous potassium carbonate solution (3.6 moles in 3 l water) and with a second potassium carbonate solution (0.4 moles in 1 l water). The combined basic aqueous layers were washed with toluene (1 l) and acidified with concentrated hydrochloric acid. The resulting solid was isolated by filtration, washed with water (2×2 l), and dried under vacuum at 50° C. to give 1008 g (58%) of a granular orange solid.

2. Preparation of methyl 3-(2',6'-dichlorophenyl)-2,3-dioxoproprionate-2-(4''-chlorophenyl) hydrazone A solution of 428 g of 4-chloroaniline (3.36 moles) in 2 l of ethanol (denatured, anhydrous) was stirred in an ice-salt bath as 586 ml of concentrated hydrochloric acid (7.04 mole) was added at such a rate that the temperature did not rise above 5° C. The solution was stirred as a solution of 238 g of sodium nitrite (3.56 moles) in 300 ml of water was added at such a rate that the temperature did not rise above 5° C. The resulting diazonium salt solution was stirred for 10 min. The stirring was stopped and the precipitate was allowed to settle. The diazonium salt was kept cold (5° C.) until use.

A solution of 924 g of methyl 2,6-dichlorobenzoylacetoacetate (3.2 moles) from step 1 and potassium acetate (3 kg, 30.6 moles) in 13 l of 95% ethanol (denatured) was stirred in an ice-salt bath (temperature 5° C.) as the above diazonium salt solution was added at once through a coarse filter. The reaction was stirred for 4 hrs. with cooling and allowed to warm to room temperature over 16 hrs. The precipitated product was diluted with 2 l of water and isolated by filtration. The solid was washed with water (2×2 l) and dried under reduced pressure at 50° C. to give 1042 g (84%) of a yellow solid.

3. Preparation of methyl 5-chloro-1-(4'-chlorophenyl)-1,4-dihydro-4-oxo-cinnoline-3-carboxylate A slurry of 376 g of potassium carbonate (2.7 moles) and 2 g of 18-crown-6 in 3.0 l of dimethylformamide was stirred and heated at 130° C as 1.0 kg of solid hydrazone (2.6 moles) from step 2 was added over 30 min. The reaction was heated at 135° C. for 1 hr. The reaction was allowed to cool to 60° C. over 3 hrs. and then cooled to 25° C. in an ice bath. The thick mixture was poured into 6 l of cold water. The resulting slurry was stirred for 30 min. before the solid was isolated by filtration, washed with water (2×2 l), and dried under reduced pressure at 45° C. to give 905 g (99%) of an off-white solid.

4. Preparation of 1-(4'-chlorophenyl)-1,4-dihydro-5-methoxyethoxy-4-oxo-cinnoline-3-carboxylic acid A solution of 255 g of potassium hydroxide (3.9 moles, pellets, 85+%) in 3.2 l of methoxyethanol was stirred at 45° C. as 450 g of solid methyl phenylcinnoline-carboxylate (1.29 moles) from step 3 was added in portions. The reaction vessel was fitted with a distillation head and placed under reduced pressure (approx. 40 mmHg). The reaction was heated at 50° C. for 1 hr., then at 65° C. for 1 hr. to distill off methanol and some methoxyethanol (total volume removed 280 ml). The distillation head was replaced with a reflux condenser and the reaction was heated between 90° C. and 110° C. for 1 hr. The reaction was allowed to cool to 50° C. before the addition of 1 liter of water and was cooled to 25° C. before the resulting slurry was poured into 4 l of a cold 0.8 N hydrochloric acid solution (3.1 moles HCl). The resulting precipitate was isolated by filtration, washed with water (2×2 l), and dried under reduced pressure at 50° C. to give 472 g (98%) of an off-white solid.

The invention now being fully described, it will be apparent to one of ordinary skill in the art that many changes and modifications can be made thereto without departing from the spirit or scope of the appended claims.

What is claimed is:

1. A method for the preparation of a substituted cinnoline of the formula:

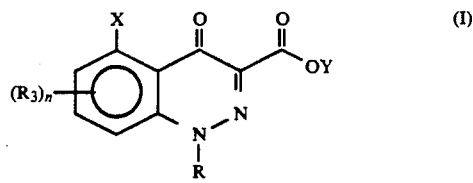

wherein X represents formula $OR_1$ or $NR_1R_2$, wherein $R_1$ represents $C_1$–$C_4$ alkyl optionally substituted with $C_1$–$C_4$ alkoxy, 1 to 3 halogen atoms, or carboxy or $C_1$–$C_4$ alkoxycarbonyl; a $C_2$–$C_4$ alkenyl optionally substituted with 1 to 3 halogen atoms; or $C_2$–$C_4$ alkynyl; and $R_2$ independently represent H or alkyl;

Y is H or $C_1$–$C_{22}$ linear alkyl or alkenyl having up to four carbon-carbon double bonds, $C_3$–$C_6$ branched alkyl or alkenyl, $C_1$–$C_4$ alkoxyalkyl, cyclohexylmethyl, halogenated $C_1$–$C_4$ alkyl, phenyl, benzyl, —$(CH_2CH_2O)_mCH_2CH_3$ in which m is an integer from 1 to 5, or —$(CH_2OR_4)CH_2OR_5$ or —$CH_2CHOR_4CH_2OR_5$ in which either $R_4$ or $R_5$ but not both represent a $C_1$–$C_{22}$ linear alkyl- or alkenylcarbonyl having up to four carbon-carbon double bonds and the other of $R_4$ or $R_5$ is H;

R is $C_1$–$C_4$ alkyl, phenyl, naphthyl, or phenyl or naphthyl substituted with one to three substituents selected from the group consisting of halogen, $CONH_2$, $C_1$–$C_4$ alkyl or haloalkyl, $C_1$–$C_4$ alkoxy or haloalkoxy, and cyano;

each $R_3$ independently represents H or $C_1$–$C_4$ alkyl, or haloalkyl, $C_1$–$C_4$ alkoxy or haloalkoxy, $C_1$–$C_4$ alkanoyl, cyano, nitro, hydroxy or halo; and n is an integer from 0 to 3; which comprises:

reacting a compound of the formula

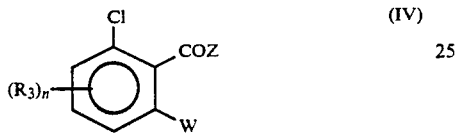

(IV)

wherein $R_3$ and n have the previously defined meanings;

W is either F or Cl; and

Z is a leaving group selected from the group consisting of H, halogen, ester, and amide leaving groups;

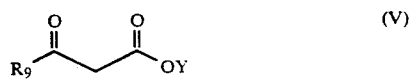

(V)

wherein $R_9$ is a hydrocarbon and Y has the previously defined meanings to form a trione of the formula

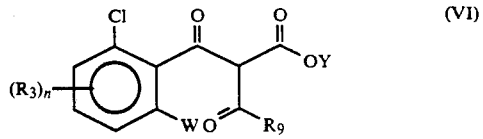

(VI)

wherein Y, W, $R_3$, R and n have the meanings as previously defined, (1) converting said trione to a dione by heating in an organic solvent, said dione compound having the formula

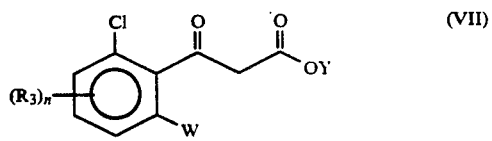

(VII)

wherein Y, W, $R_3$, and n have the meanings as previously defined, and reacting said dione with a diazonium salt of the formula $RN^+_2A^-$ wherein R has the meanings as previously defined and $A^-$ is any counter ion, to form a hydrazone of the formula

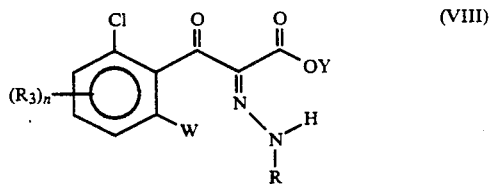

(VIII)

wherein Y, W, $R_3$, R, and n have the meanings as previously defined, or (2) converting said trione directly to the hydrazone of formula VIII by reacting said trione with said diazonium salt of the formula $RN^+_2A^-$, wherein R and A have the meanings as previously defined;

causing said hydrazone to undergo a self-condensation reaction to produce a cinnoline precursor compound of the formula

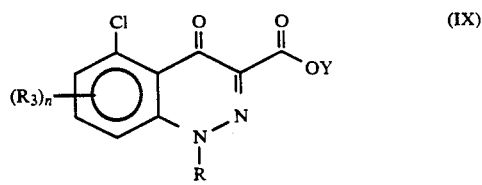

(IX)

wherein Y, $R_3$, R, and n have the meanings as previously defined, and reacting said cinnoline precursor compound with
(1) a compound of the formula
$R_1OH$ or $R_1O^-M^+$
wherein $M^+$ is a metal cation and $R_1$ has the meanings as previously defined, or
(2) a compound of the formula
$NHR_1R_2$
wherein $R_1$ and $R_2$ have the meanings as previously defined to form the desired compound of formula I.

2. The method of claim 1, wherein R represents phenyl or phenyl substituted with one to three substituents selected from the group consisting of halogen, trihalomethyl, $C_1$–$C_4$ alkoxy, $C_1$–$C_4$ alkyl, and cyano.

3. The method of claim 1, wherein Z is Cl.

4. The method of claim 3, wherein R is phenyl or phenyl substituted with a substituent selected from the group consisting of 3',4'-dichloro, 3',4'-difluoro, 4'-methyl, 4'-methoxy, 4'-trifluoromethyl, 4'-iodo, 4'-chloro, 4'-fluoro, 4'-bromo, 3+- fluoro, 3'-chloro, 3'-trifluoromethyl, 2'- fluoro, 2'-chloro, 4'- trifluoromethoxy, and 4'-cyano.

5. The method of claim 4, wherein R is phenyl or phenyl substituted with 4'-fluoro or 2'-fluoro and X is $OCH_3$.

6. The method of claim 2, wherein R is phenyl or phenyl substituted with 3',4'-difluoro and X is $OCH_3$.

7. The method of claim 2, wherein R is phenyl and X is $OCH_2CH_2CH_3$ or $OCH(CH_3)_2$.

8. The method of claim 2, wherein R is a phenyl or phenyl substituted with 4'-chloro and X is $OCH_2CH_2CH_3$.

9. The method of claim 2, wherein R is phenyl or phenyl substituted with 4'-chloro and X is $OCH(CH_3)CO_2H$.

10. The method of claim 1, wherein said compound of formula IV is a 2-(2', 6'-dichlorobenzoyl)-3-keto-3-(lower alkyl)propanoic acid ester.

11. The method of claim 1, wherein $R_9$ represents a short-chain hydrocarbon.

12. The method of claim 1, wherein $R_9$ represents an alkyl or alkenyl group having from 1 to 4 carbon atoms.

13. A method for the preparation of a substituted cinnoline of the formula:

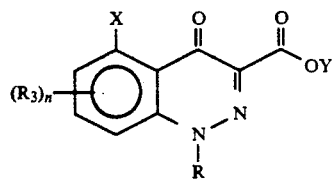
(I)

wherein X represents formula $OR_1$ or $NR_1R_2$, wherein $R_1$ represents $C_1$-$C_4$ alkyl optionally substituted with $C_1$-$C_4$ alkoxy, 1 to 3 halogen atoms, or carboxy or $C_1$-$C_4$ alkoxycarbonyl; a $C_2$-$C_4$ alkenyl optionally substituted with 1 to 3 halogen atoms; or $C_2$-$C_4$ alkynyl; and $R_2$ independently represent H or alkyl;

Y is H or $C_1$-$C_{22}$ linear alkyl or alkenyl having up to four carbon-carbon double bonds, $C_3$-$C_6$ branched alkyl or alkenyl, $C_1$-$C_4$ alkoxyalkyl, cyclohexylmethyl, halogenated $C_1$-$C_4$ alkyl, phenyl, benzyl, —$(CH_2CH_2O)_mCH_2CH_3$ in which m is an integer from 1 to 5, or —$CH(CH_2OR_4)CH_2OR_5$ or —$CH_2$-$CHOR_4CH_2OR_5$ in which either $R_4$ or $R_5$ but not both represent a $C_1$-$C_{22}$ linear alkyl- or alkenylcarbonyl having up to four carbon-carbon double bonds and the other of $R_4$ or $R_5$ is H;

R is $C_1$-$C_4$ alkyl, phenyl, naphthyl, or phenyl or naphthyl substituted with one to three substituents selected from the group consisting of halogen, $CONH_2$, $C_1$-$C_4$ alkyl or haloalkyl, $C_1$-$C_4$ alkoxy or haloalkoxy, and cyano;

each $R_3$ independently represents H or $C_1$-$C_4$ alkyl, or haloalkyl, $C_1$-$C_4$ alkoxy or haloalkoxy, $C_1$-$C_4$ alkanoyl, cyano, nitro, hydroxy or halo; and n is an integer from 0 to 3; which comprises:
reacting a compound of the formula

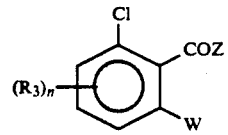
(IV)

wherein $R_3$ and n have the previously defined meanings;
W is either F or Cl; and
Z is a leaving group selected from the group consisting of H, halogen, and ester leaving groups;
with a compound of the formula

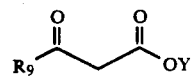
(V)

wherein $R_9$ is a hydrocarbon and Y has the previously defined meanings to form a trione of the formula

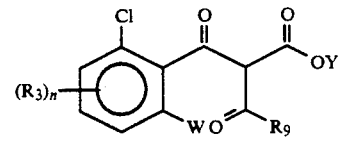
(VI)

wherein Y, W, $R_3$, R, and n have the meanings as previously defined,
(1) converting said trione to a dione by heating in an organic solvent, said dione compound having the formula

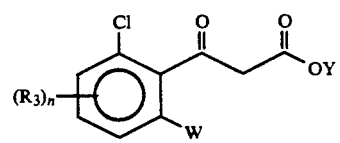
(VII)

wherein Y, W, $R_3$, and n have the meanings as previously defined,
and reacting said dione with a diazonium salt of the formula
$RN^+_2A^-$
wherein R has the meanings as previously defined and $A^-$ is any counter ion, to form a hydrazone of the formula

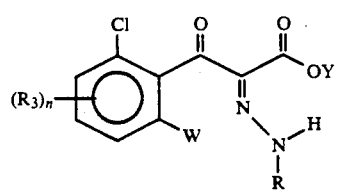
(VIII)

wherein Y, W, $R_3$, R, and n have the meanings as previously defined,
or (2) converting said trione directly to the hydrazone of formula VIII by reacting said trione with said diazonium salt of the formula $RN^+_2A^-$, wherein R and A have the meanings as previously defined;
causing said hydrazone to undergo a self-condensation reaction to produce a cinnoline precursor compound of the formula

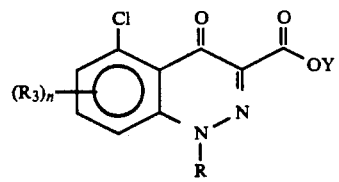
(IX)

wherein Y, $R_3$, R, and n have the means as previously defined,
and reacting said cinnoline precursor compound with
(1) a compound of the formula
$R_1OH$ or $R_1O^-M^+$
wherein $M^+$ is a metal cation and $R_1$ has the meanings as previously defined, or
(2) a compound of the formula
$NHR_1R_2$
wherein $R_1$ and $R_2$ have the meanings as previously defined to form the desired compound of formula I.

14. The method of claim 13, wherein Z represents a halogen or ester leaving group.

15. In a method for the preparation of a substituted cinnoline of the formula:

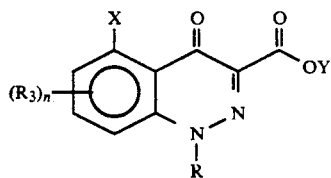

wherein X represents formula $OR_1$ or $NR_1R_2$, wherein $R_1$ is $C_1-C_4$ alkyl optionally substituted with $C_1-C_4$ alkoxy, 1 to 3 halogen atoms, or carboxy or $C_1-C_4$ alkoxycarbonyl; a $C_2-C_4$ alkenyl optionally substituted with 1 to 3 halogen atoms; or $C_2-C_4$ alkynyl and $R_2$ independently represent H or alkyl;

Y is H, alkali metal ion or $C_1-C_{22}$ linear alkyl or alkenyl having up to four carbon-carbon double bonds, $C_3-C_6$ branched alkyl or alkenyl, $C_1-C_4$ alkoxyalkyl, cyclohexylmethyl, halogenated $C_1-C_4$ alkyl, phenyl, benzyl, $-(CH_2CH_2O)_mCH_2CH_3$ in which m is an integer from 1 to 5, or $-CH(CH_2OR_4)CH_2OR_5$ or $-CH_2CHOR_4CH_2OR_5$ in which either $R_4$ or $R_5$ but not both represent a $C_1-C_{22}$ linear alkyl- or alkenylcarbonyl having up to four carbon-carbon double bonds and the other of $R_4$ or $R_5$ is H;

R is $C_1-C_4$ alkyl, phenyl, naphthyl, or phenyl or naphthyl substituted with one to three substituents selected from the group consisting of halogen, $CONH_2$, $C_1-C_4$ alkyl or haloalkyl, $C_1-C_4$ alkoxy or haloalkoxy, and cyano;

each $R_3$ independently represents H or $C_1-C_4$ alkyl, or haloalkyl, $C_1-C_4$ alkoxy or haloalkoxy, $C_1-C_4$ alkanoyl, cyano, nitro, hydroxy or halo; and n is an integer from 0 to 3;

in which an intermediate hydrazone of the formula

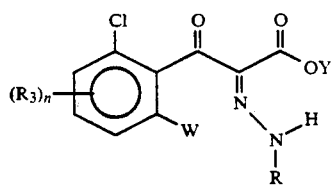

in which W is Cl or F, and Y, $R_3$, R, and n have the meanings as previously defined, is cyclized by displacement of W to form a cinnoline ring, after which Cl is converted to X, an improvement which comprises:
preparing an intermediate of formula

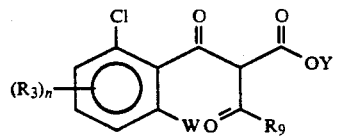

wherein Y, W, $R_3$, R, and n have the meanings as previously defined, by reacting a compound of formula

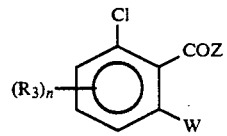

wherein W, $R_3$ and n have the meanings as previously defined;

and Z is a leaving group selected from the group consisting of H, halogen, ester, and amide leaving groups;

with a ketocarboxy compound of the formula

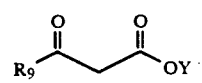

wherein Y has the meaning previously defined and $R_9$ is hydrocarbon, to form a trione of the formula

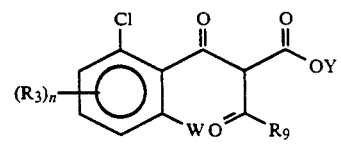

wherein Y, W, $R_3$, $R_9$, and n have the meanings as previously defined, and (1) heating said trione to form a dione of Formula VII

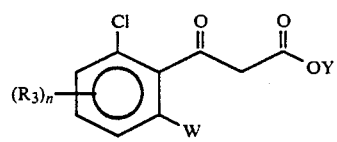

wherein Y, W, $R_3$, and n have the meanings as previously defined, and reacting said dione with a diazonium salt of the formula $RN^+_2A^-$ wherein R has the meanings as previously defined and $A^-$ is any counter ion, to form said hydrazone, or (2) converting said trione to said hydrazone by reacting said trione directly with said diazonium salt.

16. The method of claim 15, wherein heating the trione occurs at a temperature of about 50 to about 100° C. in an aqueous buffer.

17. The method of claim 15, wherein the trione is reacted with a diazonium salt of the formula $RN^+_2A^-$ wherein R represents $C_1-C_4$ alkyl, phenyl, naphthyl, or a phenyl or naphthyl substituted with one to three substituents selected from the group consisting of halogen, $CONH_2$, $C_1-C_4$ alkyl or haloalkyl, $C_1-C_4$ alkoxy or haloalkoxy, and cyano and $A^-$ represents any counter anion, to form a hydrazone having the formula (VIII)

[Structure: chlorophenyl with (R$_3$)$_n$ and W substituents, bearing a C(O)-C(=N-NHR)-C(O)-OY side chain]

and subsequently subjecting the hydrazone to a self-condensation reaction to form a cinnoline ring.

18. In a method for the preparation of a substituted cinnoline of the formula:

(I)

[Structure: phenyl ring with X, (R$_3$)$_n$ substituents, fused to cinnoline N-N(R) with C(O)-C=C-OY]

wherein X represents formula OR$_1$ or NR$_1$R$_2$, wherein R$_1$ is C$_1$-C$_4$ alkyl optionally substituted with C$_1$-C$_4$ alkoxy, 1 to 3 halogen atoms, or carboxy or C$_1$-C$_4$ alkoxycarbonyl; a C$_2$-C$_4$ alkenyl optionally substituted with 1 to 3 halogen atoms; or C$_2$-C$_4$ alkynyl and R$_2$ independently represent H or alkyl;

Y is H, alkali metal ion or C$_1$-C$_{22}$ linear alkyl or alkenyl having up to four carbon-carbon double bonds, C$_3$-C$_6$ branched alkyl or alkenyl, C$_1$-C$_4$ alkoxyalkyl, cyclohexylmethyl, halogenated C$_1$-C$_4$ alkyl, phenyl, benzyl, —(CH$_2$CH$_2$O)$_m$CH$_2$CH$_3$ in which m is an integer from 1 to 5, or —CH(CH$_2$OR$_4$)CH$_2$OR$_5$ or —CH$_2$CHOR$_4$CH$_2$OR$_5$ in which either R$_4$ or R$_5$ but not both represent a C$_1$-C$_{22}$ linear alkyl- or alkenylcarbonyl having up to four carbon-carbon double bonds and the other of R$_4$ or R$_5$ is H;

R is C$_1$-C$_4$ alkyl, phenyl, naphthyl, or phenyl or naphthyl substituted with one to three substituents selected from the group consisting of halogen, CONH$_2$, C$_1$-C$_4$ alkyl or haloalkyl, C$_1$-C$_4$ alkoxy or haloalkoxy, and cyano;

each R$_3$ independently represents H or C$_1$-C$_4$ alkyl, or haloalkyl, C$_1$-C$_4$ alkoxy or haloalkoxy, C$_1$-C$_4$ alkanoyl, cyano, nitro, hydroxy or halo; and n is an integer from 0 to 3;

in which an intermediate hydrazone of the formula (VIII)

[Structure as above with Cl and W substituents]

in which W is Cl or F, and Y, R$_3$, R, and n have the meanings as previously defined, is cyclized by displacement of W to form a cinnoline ring, after which Cl is converted to X, an improvement which comprises:

preparing an intermediate of formula (VI)

[Structure: chromanone-type ring with Cl, (R$_3$)$_n$, W, O, and R$_9$ substituents, C(O)-OY]

wherein Y, W, R$_3$, R, and n have the meanings as previously defined, by reacting a compound of formula (IV)

[Structure: chlorophenyl with (R$_3$)$_n$, W, COZ substituents]

wherein W, R$_3$ and n have the meanings as previously defined;

and Z is a leaving group selected from the group consisting of H, halogen, ester, and amide leaving groups;

with a ketocarboxy compound of the formula (V)

$$R_9-C(O)-CH_2-C(O)-OY$$

wherein Y has the meaning previously defined and R$_9$ is hydrocarbon, to form a trione of the formula (VI)

[Structure as shown above]

wherein Y, W, R$_3$, R$_9$, and n have the meanings as previously defined, and (1) heating said trione to form a dione of Formula VII (VII)

[Structure: chlorophenyl with (R$_3$)$_n$, W substituents, with C(O)-CH$_2$-C(O)-OY side chain]

wherein Y, W, R$_3$, and n have the meanings as previously defined, and reacting said dione with a diazonium salt of the formula

RN$^+_2$A$^-$ wherein R has the meanings as previously defined and A$^-$ is any counter ion, to form said hydrazone, or (2) converting said trione to said hydrazone by reacting said trione directly with said diazonium salt.

19. The method of claim 18, wherein Z represents a halogen or ester leaving group.

* * * * *

UNITED STATES PATENT AND TRADEMARK OFFICE
CERTIFICATE OF CORRECTION

PATENT NO. : 5,183,891
DATED : Ferbuary 2, 1993
INVENTOR(S) : Jeffrey Labovitz, et al.

It is certified that error appears in the above-identified patent and that said Letters Patent is hereby corrected as shown below:

Column 4, line 29, change, "-H(CH$_2$OR$_4$)CH$_2$OR$_5$" to --CH(CH$_2$OR)CH$_2$OR$_5$--.

Signed and Sealed this

Thirtieth Day of August, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,183,891
DATED : February 2, 1993
INVENTOR(S) : Jeffrey Labovitz, et al It is certified that error appears in the above-indentified patent and that said Letters Patent is hereby corrected as shown below:

Column 4, line 29, please change "-H(CH$_2$OR$_4$)CH$_2$OR$_5$" to ---CH(CH$_2$OR$_4$)CH$_2$OR$_5$--.

This certificate supersedes Certificate of Correction issued August 30, 1994.

Signed and Sealed this

Twenty-ninth Day of November, 1994

Attest:

BRUCE LEHMAN

Attesting Officer

Commissioner of Patents and Trademarks